(12) United States Patent
Prystupa

(10) Patent No.: US 8,345,254 B2
(45) Date of Patent: Jan. 1, 2013

(54) MULTIPLE PASS IMAGING SPECTROSCOPY

(76) Inventor: David Prystupa, Pinawa (CA)

(*) Notice: Subject to any disclaimer, the term of this patent is extended or adjusted under 35 U.S.C. 154(b) by 1230 days.

(21) Appl. No.: 12/669,937

(22) PCT Filed: Feb. 14, 2005

(86) PCT No.: PCT/CA2005/000181
§ 371 (c)(1), (2), (4) Date: Jan. 20, 2010

(87) PCT Pub. No.: WO2005/078414
PCT Pub. Date: Aug. 25, 2005

(65) Prior Publication Data
US 2010/0195108 A1 Aug. 5, 2010

Related U.S. Application Data

(60) Provisional application No. 60/543,918, filed on Feb. 13, 2004.

(51) Int. Cl.
*G01N 21/47* (2006.01)
*G01N 21/00* (2006.01)

(52) U.S. Cl. ........................... 356/446; 356/432

(58) Field of Classification Search ................ None
See application file for complete search history.

(56) References Cited

U.S. PATENT DOCUMENTS

| | | | | |
|---|---|---|---|---|
| 4,306,151 A | * | 12/1981 | Chase | 250/339.11 |
| 6,486,474 B1 | * | 11/2002 | Owen et al. | 250/339.02 |
| 2003/0063284 A1 | * | 4/2003 | McAndrew et al. | 356/437 |

* cited by examiner

Primary Examiner — Gregory J Toatley
Assistant Examiner — Amanda Merlino
(74) Attorney, Agent, or Firm — Ade & Company Inc; Michael R. Williams; Adrian D. Battison

(57) ABSTRACT

A method of imaging an optically thin sample is described wherein a collimated beam is directed through the sample and then reflected back through the sample one or more times. The beam is then directed toward a detector which collects and analyzes the spatial and spectral composition of the beam. In some embodiments, the detector is a focal plane array with a large number of detector elements. In other embodiments the relative position of a single detector or a small detector array and the sample is altered and the process is repeated, thereby tracing out a large virtual detector array. In either case, the spectral information received by the detector elements can be related, by methods which are elaborated below, to information about the spatial distribution of absorption in the sample.

35 Claims, 7 Drawing Sheets

MULTIPLE PASS IMAGING SPECTROSCOPY

PRIOR APPLICATION INFORMATION

This application claims the benefit of the filing date of U.S. Provisional Application 60/543,918, filed Feb. 13, 2004.

BACKGROUND OF THE INVENTION

US Patent Application 20020101587 teaches an optical system that can determine the spectra of all points in a two-dimensional scene. However, each ray only passes through the sample once; this means that many different rays pass through the same sample region at a large number of differing angles.

U.S. Pat. No. 5,818,046 teaches a combination of mid-infrared transparent elements with new element geometry, new design of the optics and a new radiation path. Specifically, radiation emerges from an IR microscope objective and is then reflected at the sample before being reflected either back to the microscope objective or to a detector. Because the radiation is focused only at a single point and is divergent everywhere else, this design is unworkable for multiple passes through a sample.

U.S. Pat. No. 6,141,100 teaches a single-bounce ATR method that is suited for optically thick, highly absorbing samples.

U.S. Pat. No. 5,965,889 teaches a single bounce, non-imaging internal reflection element which focuses divergent input radiation to a small sample area.

SUMMARY OF THE INVENTION

According to a first aspect of the invention, there is provided a method of analyzing an optically thin sample comprising:
a) directing a collimated beam through the sample;
b) reflecting the beam at a first angle of incidence back through the sample one time or more times;
c) collecting the beam with a detector array; and
d) analyzing the beam.

DESCRIPTION OF THE PREFERRED EMBODIMENTS

Figure 1:
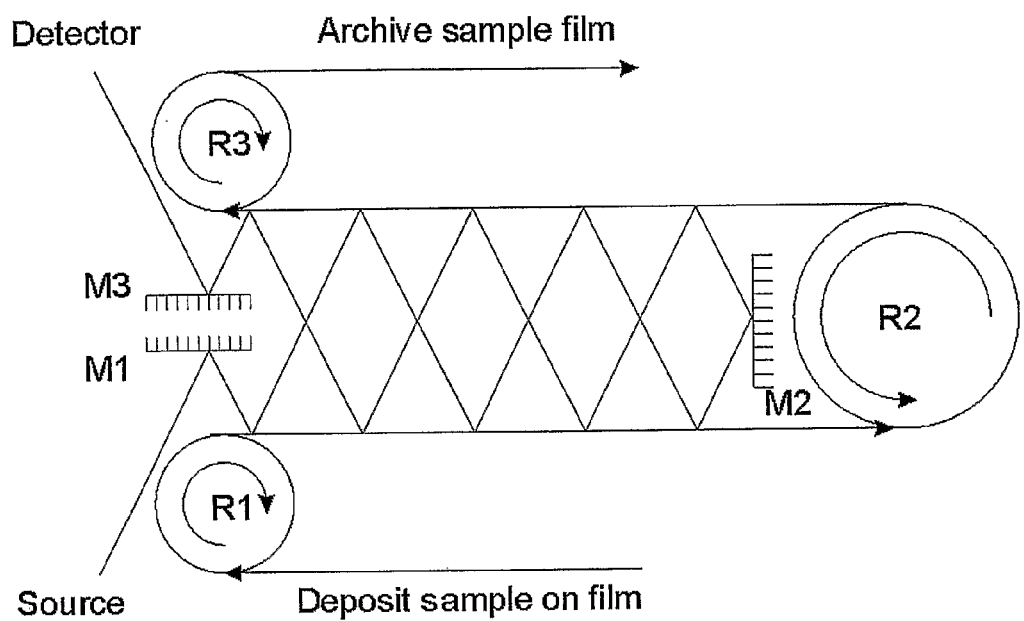
FIGS. 1 and 2 show embodiments wherein the sample is mounted on reflective tape and the tape is rolled.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a method of imaging an optically thin sample wherein a collimated beam is directed through the sample and then reflected back through the sample one or more times. The beam is then directed toward a detector that collects and analyzes the spatial and spectral composition of the beam. In some embodiments, the detector is a focal plane array with a large number of detector elements. In other embodiments, the relative position of a single detector or a small detector array and the sample is altered and the process is repeated, thereby tracing out a large virtual detector array. In either case, the spectral information received by the detector elements can be related, by methods that are elaborated below, to information about the spatial distribution of absorption in the sample. This data may be used to identify the spatial distribution of chemical components within the sample for example by pattern recognition or by comparing the data to a database, as discussed below. As discussed below, the sample may be placed or mounted on a reflective surface, or placed or mounted on a transparent or translucent surface with reflective surfaces positioned proximal to the sample for reflecting the beam. Multiple passes through the sample are used to amplify the observed signal (absorbency) into the optimal working range for the instrument, preferably 0.1 to 1.0 absorbency units. Absorbency units here have their usual meaning, namely $A=-\log(T)$, where T is the sample transmittance. The optimal number of passes through the sample is determined by the average absorbency of the sample in the frequency range of interest. This amplification of the absorbency has the benefit of improving the signal-to-noise ratio in the spectra obtained, provided that the amplification factor exceeds optical losses. This condition can be met, in general, by using good quality optical components, as discussed below.

In some embodiments, an optically thin sample refers to a sample in which the absorbency multiplied by the path length is preferably in the range of $10^{-2}$ to $10^{-6}$ absorbance units, or, in other embodiments, less. The physical thickness of such samples will depend upon the absorption coefficient in the wavelength region of interest and the density (or concentration) of the sample. For condensed phase samples, the typical thickness will be less than 1 micron in the mid infrared region. In the near infrared, optically thin samples may be millimetres thick. If the sample is gaseous, an optically thin sample may be several centimeters thick, or more. The relative benefit of the methods described herein decreases as the sample thickness increases so that little or no benefit is expected for samples thicker than about 0.1 absorbance units.

The specific geometry of each embodiment is chosen to combine the optical signals from different sample regions in a manner such that the original signals can be restored by matrix operations. The general matrix equation given below both describes well-known sampling techniques and points the way to novel sampling methods, which are the subject of the present invention.

Consider a collimated beam of electromagnetic radiation with initial intensity distribution $D_o(x, y, v)$, where x and y are coordinates perpendicular to the direction of propagation, and v is the frequency. Suppose that the beam passes though an optical system, which may include a heterogeneously distributed absorbing sample, and is normally incident upon an array of detectors numbered from 1 to N. It is of note that a single detector or small array can be made to form a large virtual array by means of relative motion between the sample and detector. Neglecting the effects of scattering, the final intensity distribution $D(x, y, v)$ will carry spatial information about the sample which is quantified by the well-known modulation transfer function. The intensity measured at the $i^{th}$ detector element ($1 \leq i \leq N$), $I_i(\nu)$ can be computed by integrating $D(x, y, \nu)$ over the area in the xy plane subtended by the detector element i. The detector element(s) is/are here assumed to be located in an image plane in a way such that the spatial information in the beam can be measured.

For the following discussion, it is convenient to refer to the pencil of rays arriving at each detector element by the index of that detector element. For example, ray i refers to that ray which terminates at detector element i. For simplicity, the path through the optical system for each ray in the incident beam may by represented parametrically. Let $\tau_i$ be the distance along the ray path arriving at detector i. Standard ray tracing methods can be used to compute the exact path for $\tau_j$. For a given $\tau_i$, it is possible to express the absorbency of the sample $\alpha(i, \tau, \nu)$ in terms of the beam coordinate system by applying appropriate coordinate transformations at each optical interface. These coordinate transformations are well known to those skilled in the art. The intensity of ray i can be computed as follows:

$$I_i(\nu) = Io(\nu) \exp\{-\int_i \alpha(i,\tau,\nu) d\tau\} \quad (1)$$

where the integral is taken over the path of ray i. Equation (1) is easily rearranged to give the absorption as $$Ai(\nu) = -\log\{I_i(\nu)\|_o(\nu)\} + C_1 = C_2 \int_i \alpha(i,\tau,\nu) d\tau \quad (2)$$

where $C_1$ and $C_2$ are constants. The path of ray i can be divided into a series of segments which either pass through the sample or do not pass through the sample. The contributions from segments that do not pass through the sample are absorbed into the constant $C_1$ and will be neglected in the following discussion. The integrals over each sample segment can be evaluated. Setting:

$$b_j = C_2 \int_j \alpha(i,\tau,\nu) d\tau \quad (3)$$

where the integral is taken over the segment j of path i, the total absorption can be expressed as $$A_i(\nu) = \Sigma_j b_j(\nu) \quad (4)$$

In general, path i does not include all possible sample segments. Furthermore, for optical systems with certain symmetries, it is possible for the path i to pass through sample segment j wholly or partially more than once. Equation (4) can, thus, be generalized as a set of matrix equations as $$A(\nu) = Cb(\nu) \quad (5)$$

where $A(\nu)$ is a column vector of absorption measured by each detector element, C is a matrix of coefficients characteristic of the optical system, and $b(\nu)$ is a column vector of the absorptivity (Equation 3) at each sample location. If there are n detector elements and m sample locations, then C will be of dimension n×m. The C matrix can be calculated as follows:

Step 1. Construct an n×m C matrix. The rows will represent logical detector regions and the columns will represent sample regions. Initialize the matrix so that all elements are zero.

Step 2. Divide the detector plane into n logical regions with a coordinate system commensurate with the symmetry of the optical system. Each detector region will be bound by p vertices (3 for triangular, 4 for rectangular/square/rhombohedral, 6 for hexagonal). The detector plane regions need not correspond to the physical detector elements at this stage. The number of logical detector regions may preferably be much larger than the number of physical detector regions. This expediency is undertaken both to facilitate calculations that exploit the symmetries of the optical system and also to account for the gaps between elements of a detector array. The number of detector regions in the C matrix will be reduced to the number of physical detector regions in Step 8.

Step 3. Divide the sample plane into m regions. The size of the sample regions should reflect the spatial resolution of the optical system. As discussed below, the shape of the sample regions should be space filling and should preferably reflect the symmetries of the optical system.

Step 4. From each vertex on the detector plane, propagate a ray through the optical system, noting the coordinates each time the sample surface is intersected. By this operation, the coordinate system of the detector plane is projected onto the sample plane and superimposed over the m sample regions one or more times.

Step 5. For each set of sample plane intersections noted in Step 4, execute Steps 6-7.

Step 6. For each row representing a detector region, execute Step 7.

Step 7. For each sample region, calculate the fraction the sample region that lies within the projected detector region. This value will range from 0.0 if no part of the of the sample region lies within the projected detector region to 1.0 if the entire sample region lies within the projected detector region. If the angle of incidence varies, the fraction should be multiplied by a factor that represents the ratio of the depth of penetration to the average depth of penetration for the system as a whole. Add each value so obtained for each sample region to the value in the column of the C matrix for that sample region. Note that the fractional area calculation can be appreciably simplified by an appropriate initial choice of coordinate system in Step 2.

Step 8. Construct a coordinate transformation matrix U, which transforms the logical detector regions into physical detector regions. If the initial choice of detector coordinates corresponds to physical detector coordinates, U will be the identity matrix/and this step may be skipped. Reduce the dimension of the C matrix with a similarity transformation ($C' = U^T C U$). The effect of the similarity transformation could be, for example, to sum several logical regions comprising a physical detector region, while at the same time omitting contributions from logical detector regions that correspond to insensitive regions of the physical detector.

The algorithm given above assumes that the geometry of the optical system is exact. In reality, the manufacturing process will introduce small deviations from the design parameters that are used in the ray tracing procedure described above. The effect of these small deviations will be to shift some of the signal expected in each detector element to neighbouring detector elements. This effect can be corrected by iteratively varying the design parameters to optimize the fit between an experimentally measured (using test patterns) C matrix and the model C matrix.

In general, the problem is to deduce the values of $b(\nu)$ from the measured $A(\nu)$ and known C. Direct methods are possible in cases where C is square and non-singular. Iterative methods could provide approximate solutions for cases in which C is not square and non-singular.

Within this framework, four classes can be identified. Class I is the trivial solution C=sI, where s is some scalar and I is the identity matrix. Most prior imaging applications fall in this class. Class II comprises all C in which n<m, plus singular matrixes of higher dimension. In this class there are more unknowns m, than observations n. It is possible, nevertheless, to obtain some information about n combinations of sample segments. Class III comprises all C that are n×n and non-singular, except scalar multiples of the identity matrix (Class I). In Class III the number of observations equals the number of unknowns and a linear solution exists. It is noteworthy that in some instances, a Class II matrix can be augmented with known values (boundary conditions) to produce a Class III matrix. The linear solution is obtained by calculating $C^{-1}$, the inverse of C. Class IV comprises all C in which n>m. In this class there are more observations than there are unknowns. Solutions to the matrix equation (5) can be obtained by using least squares or computed tomography algorithms.

To illustrate this classification scheme, specific applications and their classification are outlined below.

Case A Standard Transmittance Experiment.
Class I

In this case there is one sample segment (m=1) and one detector (n=1). The ray passes through the sample. C is the 1×1 identity matrix I.

Case B Standard External Reflectance Experiment
Class I

As in Case A, except that the ray reaching the detector has three components. Each component can be represented by a separate equation. The first component is specular reflectance from the top surface of the sample. The second component is diffuse reflectance consisting of rays scattered and absorbed several times in the sample bulk. Diffuse reflectance is measured by focussing off-specular rays at the detector. The third component, reflection-absorption, is transmitted through the sample suffering absorption as it passes through the sample. This ray reflects off a substrate, and passes through the sample again suffering absorption on the way to the detector. Because the rays pass through the sample twice, the coefficients of the C matrix are 2.0. The relative importance of each component depends upon the sample and experimental conditions.

Case C Standard Internal Reflectance Experiment
Class II

There are many sample segments (m≧1), each one corresponding to an internal reflection at the sample interface. There is one detector (n=1). C is the 1×m row vector in which every coefficient is 1.0. Cb(v) is effectively a dot product which is the sum of absorbencies of each sample segment.

Case D Multiple External Reflectance
Class II

The reflection-absorption component is here assumed to dominate. There are multiple sample segments (m>1), each one sampled once. There is one detector (n=1). C is the 1×m row vector in which every coefficient is 2.0. Cb(v) is effectively a dot product which is the sum of absorbencies of each sample segment.

Case E Standard Mapping Experiment
Class I

This case is the same as standard transmittance or standard reflectance, except that the detector and sample may move relative to one another to simulate an array of detectors.

Case F Standard Transmittance Imaging Experiment
Class I

There are many sample segments (m≧1). There is a one-to-one correspondence between each sample segment and a detector element (n=m). C is an n×n identity matrix I.

Case G Standard External Reflectance Imaging Experiment
Class I

The reflection-absorption component is here assumed to dominate. This case is the same as Case B, except that there are many detector elements. There is a one-to-one correspondence between each sample segment and a detector element (n=m). C=2I.

Case H Standard Internal Reflectance Imaging Experiment
Class I

Each sample segment is sampled once (1 bounce ATR). There are many detectors (n>1). There is a one-to-one correspondence between the sample segments and detector elements (m=n). C is an n×n identity matrix I.

Case I White Cell
Class II

There are many sample segments (m>1), which represent multiple passes through a homogeneous (usually gaseous) sample. The number of passes multiplies the absorption of a single pass. There is one detector (n=1).

Case J Resonant Cavity
Class II

The sample is placed inside a laser resonator. The number of sample segments approaches infinity. The output signal depends upon the gain and the sample absorption. One detector is used.

Case K Multiwell Devices
Class I

Multiwell devices are variants of standard transmission imaging and standard reflectance imaging in which multiple samples are confined within an array of cells.

Case L Computed Tomography
Class IV

There are many detectors (n>1). There is one sample segment per detector (m=n). The set of ray integrals (e.g., 1) for each angle of incidence is called a slice. A typical data set contains 180 to 360 slices, each slice corresponding to a different angle of incidence. The distribution of absorbency in a slice is calculated by using a Radon transform (The Radon transform defines the argument in a Fourier transform.) Computed Tomography gives an indirect estimation of the two- or three-dimensional distribution of absorbency.

Case M Cyclic Reflectance
Class III

There are many detectors (n>1). There are many sample segments per detector (m=nl, l=1, 2, 3 ... ), but only n unique sample segments. Each ray passes though several sample segments. The angle of incidence is the same for each sample pass. The distribution of absorbency in the sample is computed directly by $$b(v)=C^{-1}A(v).$$

The optical probe is primarily intended to facilitate infrared spectroscopic imaging of optically thin, heterogeneous samples. Multiple passes through the sample are used to amplify the observed signal (absorbency) into the optimal working range for the instrument, typically 0.1 to 1.0 absorbency units. The optimal number of passes through the sample, and hence the amplification required, is determined by the average absorbency of the sample and the optical losses incurred by the amplification process. This amplification of the absorbency has the benefit of improving the signal-to-noise ratio in the spectra obtained, provided that the amplification factor exceeds optical losses. This condition can be met, in general, by using good quality optical components.

The general principle behind the improvement in the signal-to-noise ratio is outlined below. Several simplifying approximations are used; the purpose here is to illustrate the principle rather than to derive an exact formula. Those of ordinary skill in the art can easily derive a more detailed model. Suppose that there are n sample reflections and m non-sample reflections. For simplicity, assume that the reflectivity, R, is the same at each surface. Because the sample is optically thin, absorption losses are small compared to reflection losses and are neglected here. The signal due to sample absorption will increase in proportion to n. The optical throughput, however, will be proportional to $R^{m+n}$ and the signal-to-noise ratio will scale as the square root of this number. Combining factors, the gain due to multiple sample passes is approximately proportional to $nR^{(m+n)/2}$. As an example, assume m=n=5. In this case the reflectivity must be 72.5% just to achieve gain=1.0 (breakeven). If the reflectivity increases to 98%, which is a typical value for a good quality gold or silver mirror, the gain increases to 4.52, or approximately 90% of the number of sample reflections. If the reflectivity is 100%, as is the case for an internal reflectance element, the gain is equal to the number of sample passes.

In general, each ray arriving at a detector element passes through several different sample segments. Conversely, each sample segment has enough rays passing through it to ensure that C is non-singular. Non-singularity can be ensured either by the inherent symmetry of the sampling system or by setting boundary conditions. It can be shown that the value of the determinant of the C matrix for a cyclic group of measurements is equal to the number of sample passes, provided that the number of sample regions is greater than the number of sample passes. The non-zero determinant guarantees that C is invertible and, thus, that image reconstruction via a linear transformation is possible. A group of translations has the property in common with cyclic groups that an operator will produce successive elements of the group. If the translations are in a flat plane, the set of translations lacks an operator relating the first and last elements of the group and is not cyclic. (The set of translations around a closed loop is cyclic, however.) In general, the C matrix for a set of translations is singular. The matrix can, however, be made non-singular by the application of reasonable boundary conditions, specifically that certain sample regions contribute zero absorbency. Because the C matrix is based on cyclic, or approximately cyclic operation, we coin the term cyclic reflectance to describe this special case.

Note: Cyclic groups are composed of a set of elements and an operator to transform one element in the set into another element in the set. For example, the set of rotations {0, 30, 60, 90, 120, 150, 180, 210, 240, 270, 300, 330}, together with a 30 degree rotation operator form a cyclic group. If the operator is applied to the last element of the set, 330 degrees, the result is the first element of the set, 0 degrees.

As noted above, C is, or can be made, non-singular for sampling schemes based upon translational and rotational symmetries. The combinations of these symmetries which fill space are termed space groups. A complete listing of all possible space groups is given in the International Tables for X-Ray Crystallography. By using a sampling scheme based on one of the 230 space groups, we can guarantee that every part of a sample is scanned. While the space group symmetries are clearly preferred, we do not exclude the possibility that a sampling scheme based on another space-filling symmetry, for example but by no means limited to Penrose patterns, may have utility.

Preferred Implementations of Cyclic Reflectance

As noted above, optical losses at each optical component are an important design consideration in the implementation of the optical probe geometry. The use of embodiments with fewer optical components can reduce optical losses. Embodiments can be classified according to the number of reflections required per pass through a sample region. The preferred implementations require one, two, or three reflections per sample pass.

One Reflection Per Sample Pass Geometry.
(A) Radiation is directed via steering optics onto a reflective strip of film (a tape) upon which optically thin samples have been deposited. The tape may additionally include optical, magnetic, or other encoding about the sample and the tape location proximate to the sites of sample deposition. The tape is bent around a sprocket through 180 degrees at least once. The part of the tape before the sprocket is anti-parallel to the part of the tape after the sprocket. Radiation follows a zigzag path between the two parts of the tape until it is intercepted by steering optics, which direct the radiation to a detector array. Successive measurements are made as the tape is translated. If there are N reflections, then the first N−1 sample regions will be empty in order to set boundary conditions on the C matrix. This is a minor restriction because N will generally be less than 10, whereas the total number of sample regions on the tape could exceed $10^6$. The empty regions in this case are essentially a background measurement and for large N it may be advantageous to alternate sequences of sample and empty (background) regions. See FIG. 1.

(B) As in (A), except that the tape forms a closed loop. This is a proper cyclic group so no boundary conditions are required. See FIG. 2.

(C) As in (A), except that the tape passes around a series of sprockets arranged in a regular polygon. The incident rays make the same angle of incidence with each successive face of the polygon.

(D) As in (A), (B), or (C) above, except that the interior region contains an internal reflection element. A refractive-index matching lubricant may optionally be placed between the IRE and the tape. Optionally, rollers may be placed on the tape to ensure good and uniform contact between the IRE and the tape.

(E) The sample is deposited on an optically transparent substrate held between two reflective surfaces. Examples of suitable substrates include, but are by no means limited to, alkali halide salts, glasses, very thin polymer films and aerogels.

(F) As in (E) except that the sample is entrained in, or suspended by, an optically transparent gas or liquid. In one embodiment, a sample particle may be entrained in a laminar flow, as in a flow cytometer. In another embodiment, a small particle, such as a spore, is suspended by a flow of air.

(G) As in (F), except that the sample is held in position by electromagnetic forces. In one embodiment, a laser may generate the electromagnetic forces (optical tweezers).

(H) As in (F), except that sample is gaseous.

Method for Preparation of Biological Samples on a Tape.

The method here described allows optimal utilisation of the detection apparatus. In a concentrated randomly distributed sample, it is possible for two or more cells to lie within the same detection region. Here a detection region refers to the smallest region that can be spatially resolved by the apparatus. In a well-designed optical system, the spatial resolution is ultimately limited by diffraction to a value close to the wavelength used. The specific size of the detection region will depend upon the wavelength of the radiation and the optical components. If the cells are different, this circumstance will make the cell classification problem more difficult. If the sample is dilute, then the cells will most likely lie in different detection regions, but the detector elements will be underutilised. Because the detector elements are the highest cost component in the detection apparatus, full utilisation is desirable. The optimal sample will have one cell per detection region, with 1-2% of the detection region left empty to determine the background, as discussed below.

An aqueous suspension of cells is passed though an apparatus that isolates individual cells in small water droplets. In one embodiment the apparatus is a flow cytometer. Alternately, the apparatus may be a modified piezo ink jet. The stream of droplets is incident upon a normally closed gate that deflects droplets containing water only to a waste bin. When a droplet containing a cell is detected, the gate opens allowing the droplet to strike a tape within a precisely determined region. At the same time, information about the mass of the cell, previously determined by a capacitance measurement, and a unique identifier are encoded on the film proximate to the cell location. The cell mass is used in three contexts. First, the cell mass provides a means to detect multiple cells in a single droplet, which will occur occasionally. Secondly, the cell mass may be used to discriminate between prokaryotic (e.g., bacteria) and eukaryotic (e.g., mammalian) cells so that only the pre-specified type of interest is measured. In a meat packing plant, for example, it may be of interest to know whether or not *E. coli* O157 is present in wash water. The presence of mammalian cells is of no interest in this case. Thirdly, the cell mass correlates with the age and growth phase of the cell, and can, thus, be used together with the spectral information to identify the type of cell (for a pattern recognition algorithm, the mass can be treated as another spectral data channel). The film may optionally contain a layer of growth medium appropriate to support the types of cells anticipated. An optically thin layer may optionally be placed on top of the film in a second process for the purpose of encapsulating hazardous organisms. The tape may be either reflective or transmissive, depending upon the preferred method of spectroscopic measurement.

Two Reflection per Sample Pass Geometry.

In the two reflection per sample pass geometry, radiation reflected from the sample is reflected onto another region of the sample with a single optical element. The case in which the radiation is reflected back along its original path is excluded from the present consideration because of two limiting factors—only two sample passes are possible and a beamsplitter is required.

(A) The simplest geometry for external reflectance measurements consists of a plane mirror located parallel to a sample plane. Rays initially incident on the sample zig-zag between the sample and mirror, finally exiting at the end of the mirror and being directed to a detector array. Successive measurements are made as the sample is translated. If there are N sample reflections, the first N−1 sample regions should be empty to set the boundary conditions on the C matrix. A variation on this concept is given in FIG. 3.

(B) An array of mirrors is arranged around the vertices of a regular polygon. Rays initially incident on the sample are reflected to vertices of a similar polygon on the sample surface. The spacing between the vertices on the sample surface should be an integer multiple of the reduced beam diameter. The preferred geometries are trigonal, square, and hexagonal. The reduced beam diameter is defined as the diameter at which complete overlap of adjacent beams occurs. The input beam may be shaped to match the polygon symmetry. The mirrors at each vertex may be visited sequentially or non-sequentially. See FIG. 4.

(C) As in (A) or (B), except that the sample and mirror(s) are located in faces of an internal reflection element. A variant of this concept, which includes rollers to ensure sample contact, is given in FIG. 5.

(D) As in the three-reflection case (A) below, except that the sample is mounted on an optically transparent substrate. The range of embodiments is described in cases (E), (F), (G) and (H) above for the one reflection geometry.

Three Reflection Per Sample Pass Geometry.

In the three-reflection per sample pass geometry, radiation reflected from the sample is reflected onto another region of the sample with two optical elements. The number of possible arrangements is vast, but discussion will be limited to a special case.

(A) Rays initially incident upon a sample region are reflected by mirror 1 to mirror 2, which directs the rays to the same sample region at the same angle of incidence, but from a different direction. This process may be repeated many times, the practical number being determined by spatial constraints and optical losses at each mirror face. While the central ray of each reflected beam strikes the sample in the same place, non-central rays are inverted and rotated. The absorbency of the sample seen at the detector is a superposition of several inverted and rotated images of the sample superimposed. The angles of rotation can be chosen such that the images form a cyclic group and C is non-singular.

Figure 6:
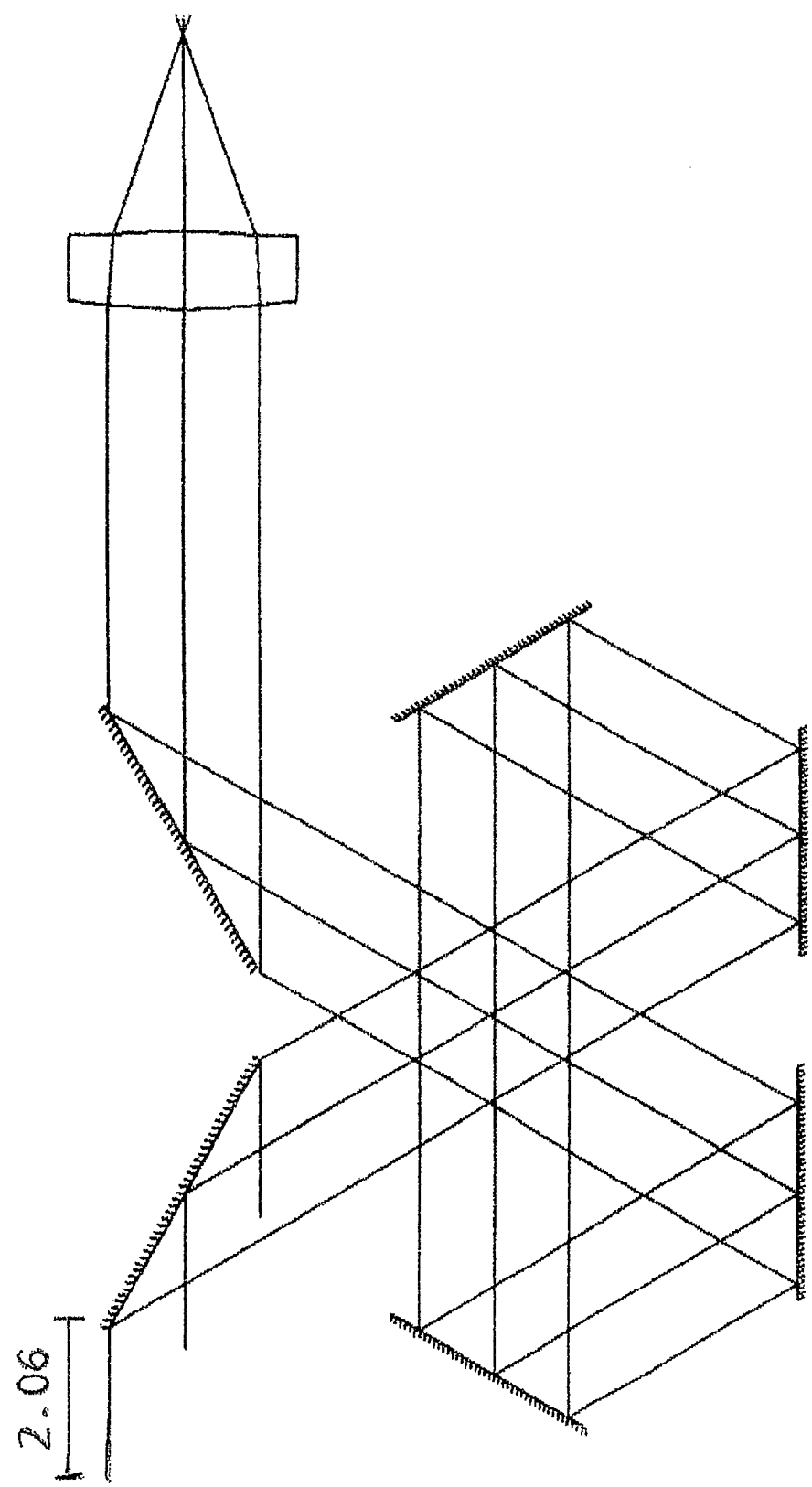
FIG. 6 shows an embodiment wherein the beam is reflected through the sample three times from different directions.
Figure 7:
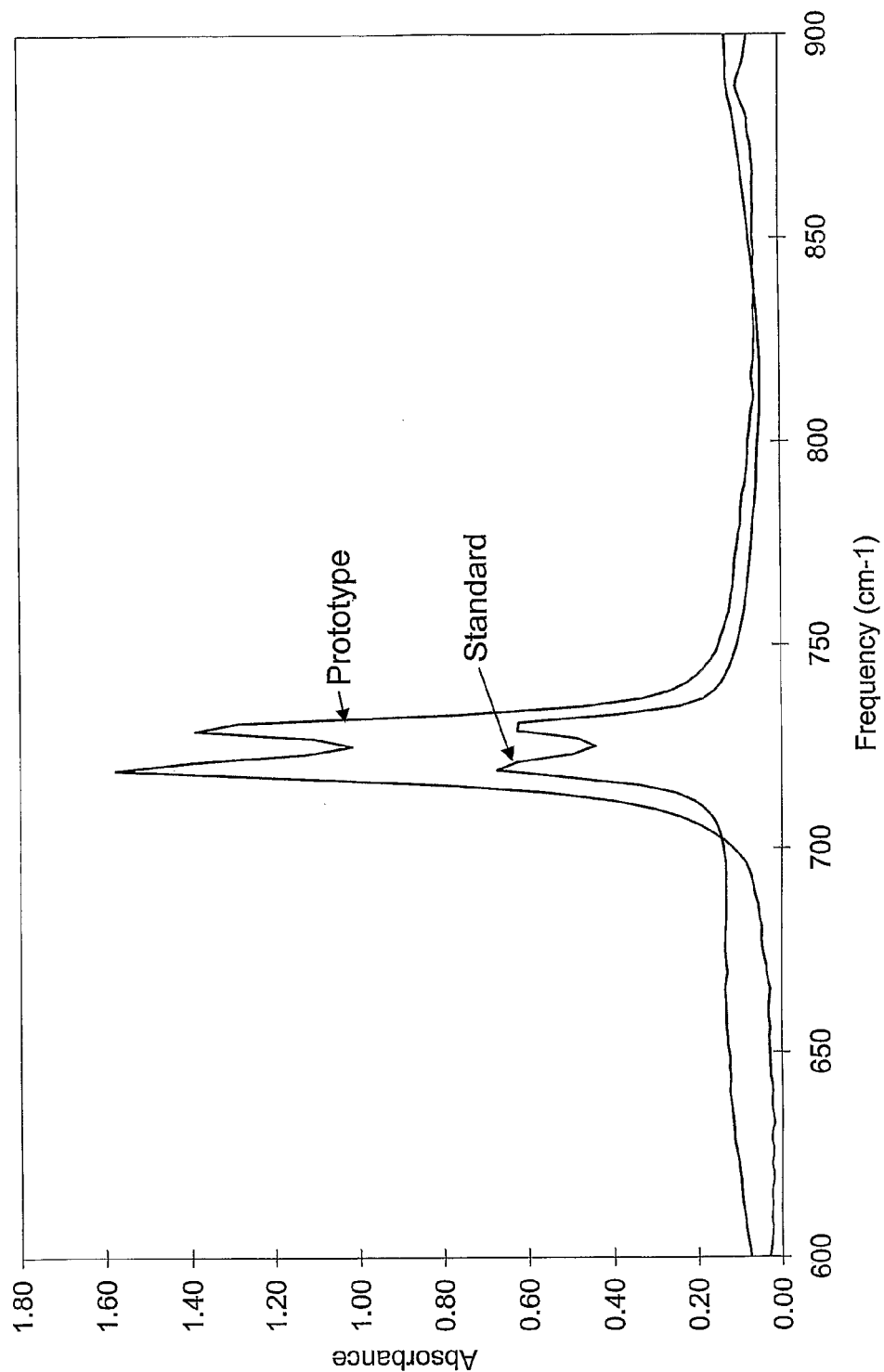
FIG. 7 shows the spectrum of a polymer film obtained with the embodiment shown in FIG. 6.

An example wherein the rays strike the sample 3 times is given in FIG. 6. Note that the mirrors are inclined to the plane of the diagram such that a ray from the sample to a mirror is reflected to the next mirror parallel to the sample plane. In a prototype, the angle of inclination is 60°. FIG. 7 gives the mid infrared spectrum of the same polymer film measured at 60° incidence using a conventional reflectance accessory (lower curve) and the design given in FIG. 6 (upper curve). The spectra shown are raw data. The three-fold enhancement of the integrated absorption is clearly evident.

(B) As in (A) except that the sample and mirror faces are the facets of an internal reflection element.

It is noteworthy that the three reflection per sample pass geometries do not require translation or rotation of the sample (or equivalently of the source beam), and is therefore preferred for samples that could be altered by movement.

Cyclic Reflectance provides a method for achieving the optical amplification of traditional non-imaging multi-reflection in an imaging context. In spectroscopic applications the best achievable signal-to-noise ratio is determined predominantly by electronic noise in the detector, which is fixed. As discussed previously, Cyclic Reflectance will generally reduce the optical throughput, but the amplification more than makes up for this loss. If good quality optical components (>98% reflectivity) are used, the improvement in the SNR is approximately 90% of the number of sample reflections (i.e., 10 reflections produces a 9-fold improvement in the SNR).

In general, the signal from a small region of the sample is recorded in a single detector channel using conventional imaging and in several detector channels using cyclic reflectance. If the detector array is imperfect or damaged, parts of the image will be missed using conventional imaging. Using cyclic reflectance, however, the effect of missing detector channels is to degrade the SNR of several image pixels. This capability to continue functioning despite damage to a part of the detector array makes cyclic reflectance more suitable than conventional imaging for use in hazardous environments. Examples of hazardous environments where cyclic reflectance may be employed include, but are by no means limited to (i) field inspection of oil wells or gas transmission pipelines, (ii) detection of chemical or biological agents for civil defense or military applications, (iii) and monitoring a chemical manufacturing process.

Cyclic Reflectance is a method for measuring ray integrals (equation 1) which are used as the basis of computed tomography (CT) calculations. The data from one Cyclic Reflectance measurement corresponds to one slice of data. Cyclic Reflectance can, thus, be used as a preliminary step for a CT application as a way to improve the signal-to-noise ratio (SNR) of the data. Cyclic reflectance will be of particular benefit for imaging weakly absorbing media, such as a small volume of gas in a combustion chamber. Another instance where cyclic reflectance may aid CT measurements is near infrared (NIR) imaging of small objects such as a cell or a kernel of wheat.

While the preferred implementations utilize multiple instances of the same angle of incidence, all that is strictly required for the purpose of solving equation 5 is that the sum of the angles of incidence be a constant. For example, a three-bounce sequence for a ray integral could be 40+40+40=120 (preferred) or 30+40+50=120 (acceptable).

Incoherent illumination is preferred. By incoherent illumination, we mean that there is no correlation between the phases of wave trains leaving adjacent points of the source (spatial incoherence) and there is no correlation between the phases of wave trains leaving the same point on the source at different times (temporal incoherence). If the illumination is incoherent, then the time-averaged signal at the detectors will not display interference effects. With the exception of the central point in the three reflection per sample pass geometry, rays do not pass through the same sample region and, thus, will not interfere via temporal coherence. If the illuminating radiation has a high degree of spatial coherence, each component frequency will have a set of interference fringes in sample regions that are intersected by multiple rays. Inducing high frequency changes in the optical path length with ultrasonic waves can neutralize this effect.

In the preferred implementations, the angle of incidence is the same for each sample pass, but the direction of approach varies. Information about preferred orientation perpendicular to the sample plane will be preserved. Information about preferred orientation in the sample plane will be lost.

The enhancement due to cyclic reflectance should not be confused with surface enhanced infrared absorption spectroscopy. The two effects are distinct and, in some cases, can be used synergistically to achieve very high sensitivity. So that the surface roughness does not make a significant contribution to scattering losses, the surface roughness, which contributes to the surface enhancement effect, must be of a much smaller length scale than the wavelength of the incident radiation. As noted previously, the amplification achieved by cyclic external reflectance depends sensitively upon the reflectivity of the sample. In order to increase the sample reflectivity, in some embodiments, the substrate will be metalized with one of Cu, Ag or Au in either colloidal form or as a thin vacuum-deposited coat. The surface may contain irregularities on a scale of tens to hundreds of nanometers which are conducive to the surface enhancement effect, yet still may be highly reflective to the micron range wavelengths at which infrared measurements are made.

Figure 2:
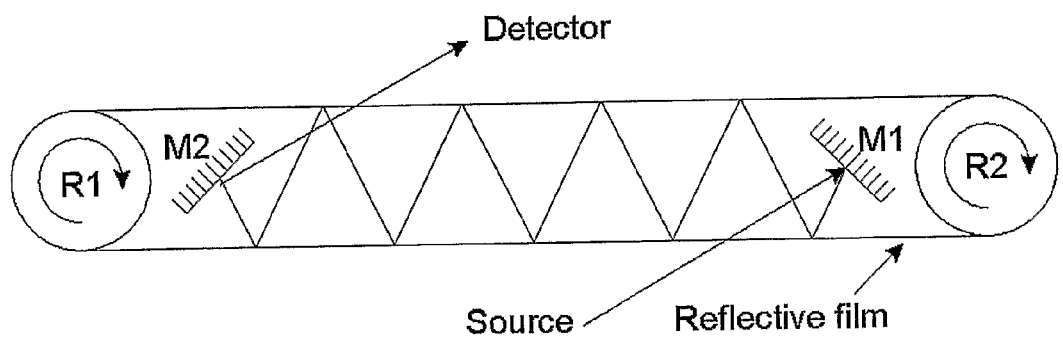
Figure 3:
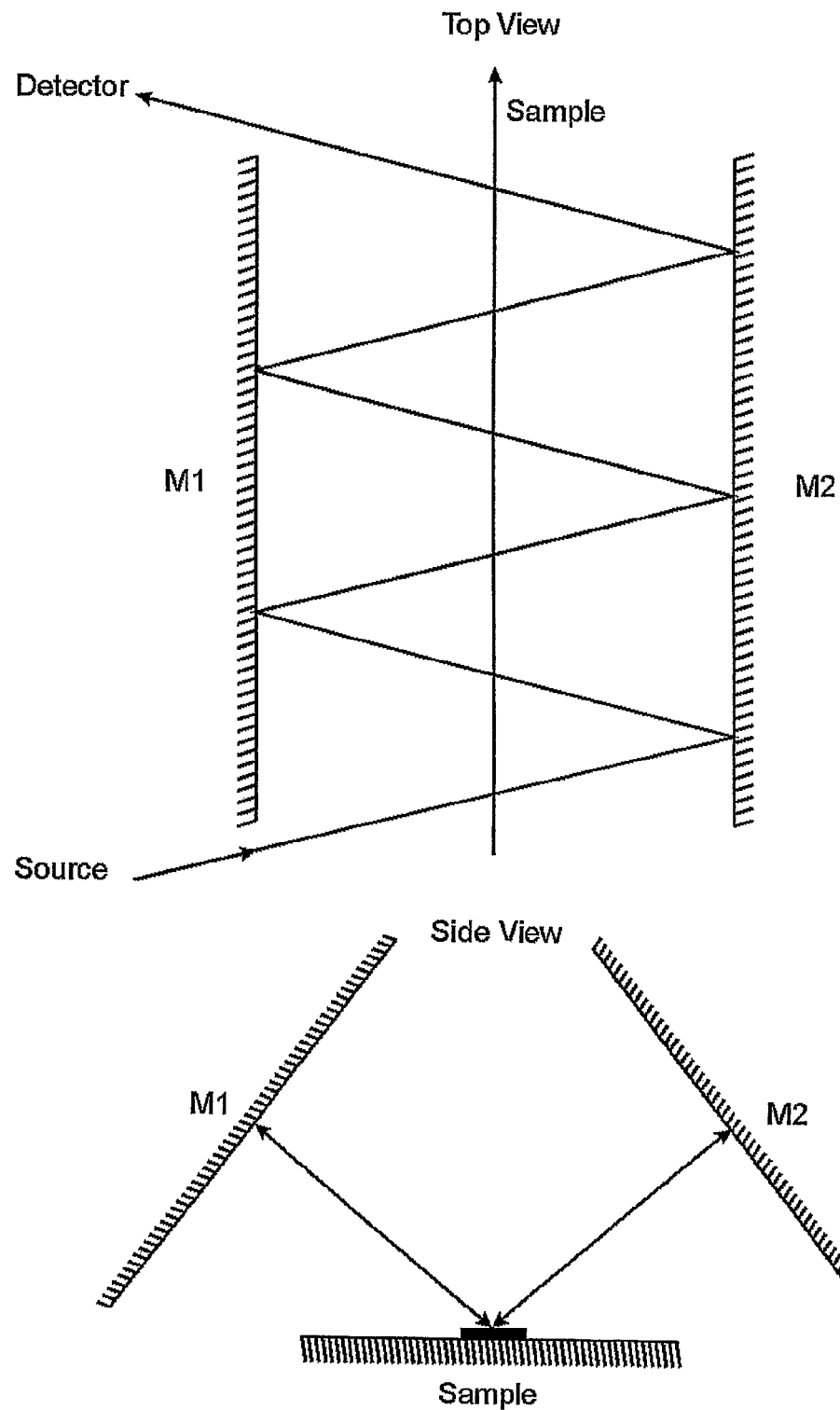
FIG. 3 shows an embodiment wherein the sample is effectively in a box composed of reflective material.
Figure 4:
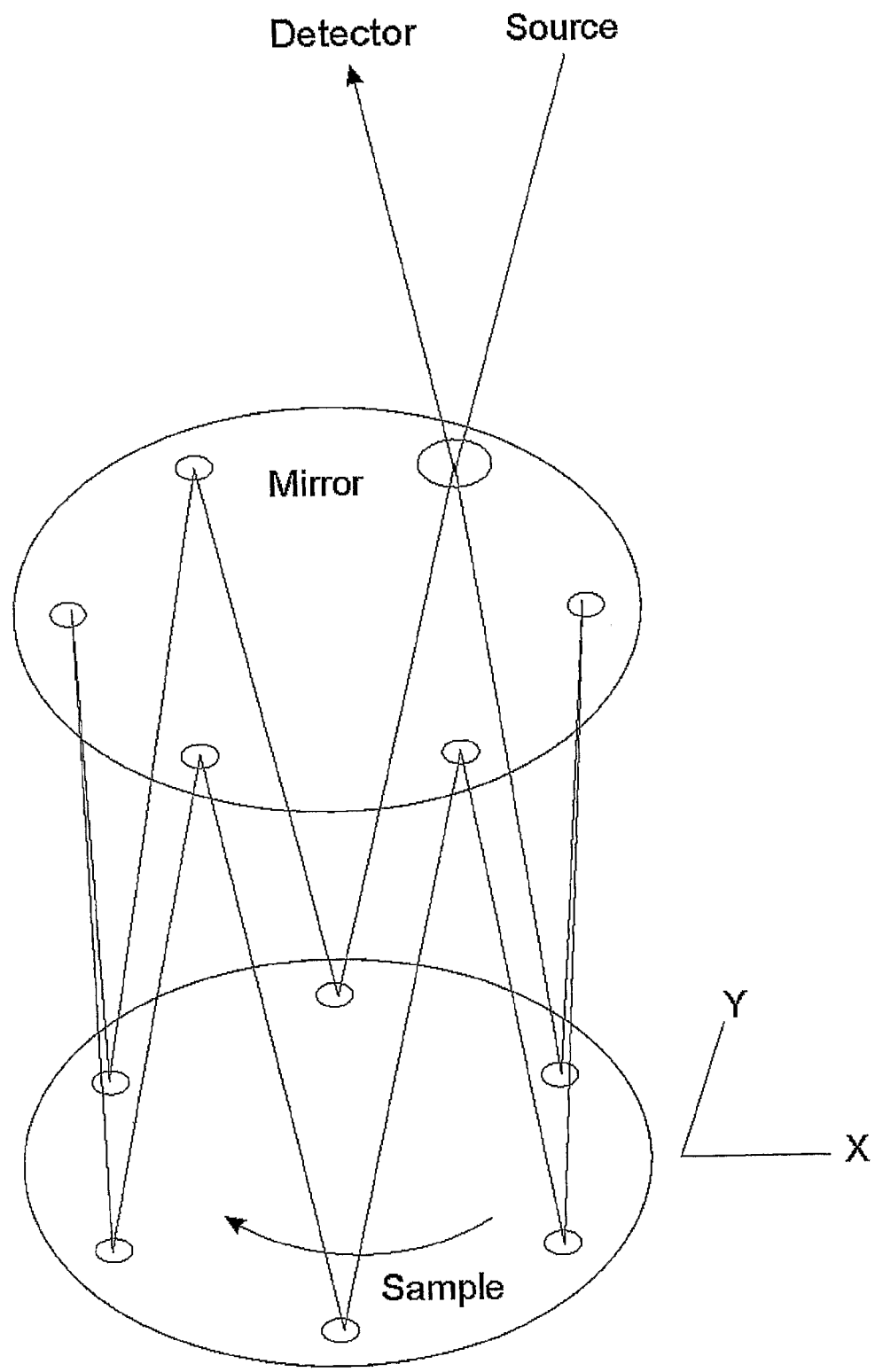
FIG. 4 shows an embodiment wherein a reflective surface is placed above the sample.
Figure 5:
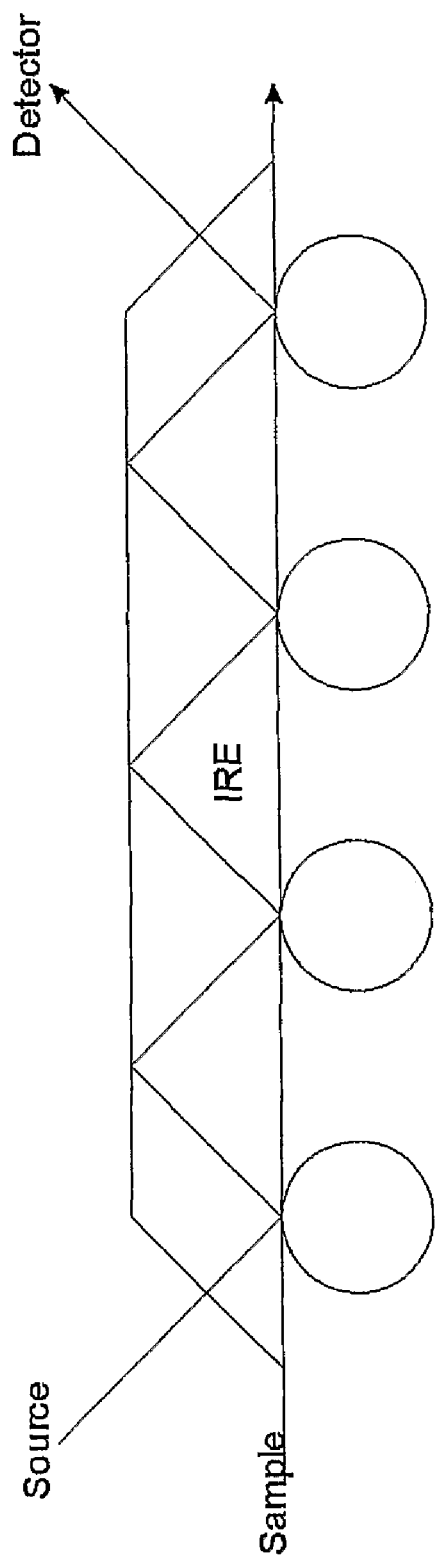
FIG. 5 shows an embodiment that incorporates a standard trapezoidal internal reflectance element.

As noted above, the sample may be mounted or placed onto a reflective surface. In some embodiments, a single steering mirror controls the angle of incidence for the incident beam. In these embodiments, the beam is incident perpendicular to the surface, or alternately at an angle large enough to ensure that the beam is not obstructed by the surface. The beam is rotated by the steering mirror into the plane of the surface and onto the surface at the desired angle of incidence. The accompanying figures show possible arrangements for sample analysis. FIGS. 1 and 2 show embodiments wherein the sample is mounted on reflective tape and the tape is rolled. FIG. 3 shows an embodiment wherein the sample is effectively in a box composed of reflective material. FIG. 4 shows an embodiment wherein a reflective surface is placed above the sample. FIG. 5 shows an embodiment that incorporates a standard trapezoidal internal reflectance element. FIG. 6 shows an embodiment wherein the beam is reflected through the sample three times from different directions. It is to be understood that these figures are for illustrative purposes only and that other suitable arrangements, which direct the beam to pass through the sample more than once, could be used within the scope of the invention.

Reflective substrates are required for external reflectance measurements only. For internal reflectance measurements, any flat, smooth substrate will suffice. There are two types of reflective surface, those which have a sample overlaid and those which do not have a sample overlaid. Those which do not have a sample overlaid are front surface metallic mirrors of conventional design, or the internal faces of a high refractive index crystal. In preferred embodiments, the reflectivity of these surfaces may be >95%. It is of note that required surface reflectivity is a function of the number of reflections. For most practical applications the surface reflectivity must exceed 50% in the wavelength range of interest. Reflectivity values below a critical value, which can be calculated for each embodiment, will decrease rather than increase signal-to-noise ratio.

For external reflectance measurements, the sample may be mounted on a polished metallic surface where the metal is selected from the group consisting of Au, Ag, Cu, Al, and Ni. Alternately, the surface could be an optically flat polymer film onto which a thin metallic layer of Au, Ag, Cu, Al or Ni has been deposited, for example as is the case with aluminised mylar. Alternately, the surface could be optically flat glass onto which a thin metallic layer has been deposited. Alternately, the surface could be an optically flat porous polymer material onto which a thin metallic layer has been deposited. Alternately, the surface could be an optically flat substrate material made reflective by treatment with Au, Ag, or Cu flakes or colloids. It is important to note that the dimensions of the colloids must be much smaller than the wavelength of the probe radiation. For mid-infrared probe radiation, the diameter of the colloids should be preferably less than 500 nm. Colloids comparable in size to the wavelength of the probe radiation form an absorbing, rather than a reflective layer. Because flakes have different resonant frequencies than spheres, this size restriction does not apply to flakes; reflective (R>50%) layers may be formed even when the linear dimensions of the flake are comparable to the wavelength of the probe radiation. In one embodiment of this concept, the substrate material is a water solution, which may contain nutrients to support cells. The metallic flakes or colloids self-assemble to form a reflective film, known in the literature as a liquid mirror. The reflectivity, on the order of 80%, is sufficient for cyclic reflectance, but not optimal. While Ag flakes or colloids have undesirable anti-microbial properties, depositing a thin layer of silica on the colloid surface can neutralize this effect. In a related embodiment, the substrate material could be a gel, such as a standard microbiological media. The gel mirror is prepared by placing a thin layer of water on the gel, forming a liquid mirror, and then allowing the gel to absorb excess water. Experiment has shown that a gel mirror prepared in this fashion is capable of sustaining an *E. coli* culture. Alternately, the surface can be sintered metal. While sintered metal surfaces remain a possibility, the secular reflectivity of sintered metal surfaces was found to be too low to be practical in preliminary experiments. Alternately, the surface could be a smooth environmental surface such as glass, stainless steel, ceramic tile, or latex paint. For these environmental surfaces, the useful wavelength range is small and the angle of incidence must be high. Although these materials are strongly absorbing (except steel) at mid infrared wavelengths, there is a small window of high reflectivity in the vicinity of strong absorptions, which can be predicted by the Krammers-Kronig relation. Glass is generally very strongly absorbing below about 1500 $cm^{-1}$. There is an associated peak in spectral reflectivity, which may make measurement of the protein Amide II band feasible by cyclic reflectance.

In some embodiments, the range of suitable angles of incidence at the sample ranges from 30 to 60 degrees. Suitable angles of incidence are selected as follows. Suppose that the sample is in the xy plane with a normal in the z direction. Let the incident beam have a circular cross section with diameter d and propagate along an axis in the xz plane making an angle θ with the normal. The projection of such a beam in the xy plane will have an elliptical shape with maximum extent d in the y direction and maximum extent $d/\cos(\theta)$ in the x direction. If the projected beam is too eccentric, then it is difficult to arrange multiple overlapping sample passes required for cyclic reflectance. For this reason, the maximum practical angle is about 60 degrees. At the low end, there are two constraints. Firstly, a small angle would require the steering reflection planes to be unacceptably small and too close together. The steering reflection planes must be at least as large as the beam diameter. The second constraint applies to internal reflectance designs. Specifically, the angle of incidence must be greater than the critical angle for total internal reflection. Taking the refractive index of the sample to be approximately 1.4, the critical angle is 20.5 degrees for Ge and 35.7 degrees for ZnSe. Furthermore, the depth of penetration should be matched to the sample thickness so as to maximize the signal from the sample and minimize the contribution from the substrate. A typical rod-shaped bacterium has a diameter of approximately 1 micron and length of 4 microns. The optimal depth of penetration is, thus, approximately 1 micron. Again, assuming that the refractive index of the bacterium is 1.4, the required angle of incidence for ZnSe is 62 degrees and the required angle of incidence for Ge is 32 degrees.

A collimated beam is used within the invention for three major reasons. Firstly, the cross sectional area of the beam at each reflection from the sample should be the same to keep the mathematical treatment simple. One could adjust for variation in radiance, but it is not certain that the C matrix would be well behaved. A variation in the cross sectional area of the beam would tend to render the redundant sampling scheme less effective. Secondly, a collimated beam guarantees that the angle of incidence is a constant, or at least distributed over a very narrow range of a few milliradians. This means that the interaction with the sample is the same over the cross section of the beam. For internal reflectance, this means that the depth of penetration is well defined and results are easily transferred from one instrument to another. This is in contrast with existing imaging ATR microscope designs that focus a beam through the IRE onto the sample. Typically, rays having angles of incidence between 20 and 60 degrees may reach the detector. The depth of penetration is a function of the angle of incidence and the relative refractive indexes of the sample and IRE. The effective depth of penetration in existing designs will be a complex integration over the distribution of angles of incidence weighted by intensity. Clearly, the results obtained will be specific to the instrument on which they were obtained. Thirdly, a collimated beam is the simplest design to implement. If the beam were focused prior to each sample pass, the number and complexity of the optical elements would increase. One of the main limitations of the effectiveness of cyclic reflectance is the optical loss suffered upon each reflection. These losses would increase if the number and complexity of optical elements increased.

In some embodiments, it is advantageous to replace the experimentally measured reference spectrum with a reference spectrum generated by an analytical model. The reason for this is that the transmittance, calculated as the ratio of the sample and reference spectra, contains noise from both sample and reference measurements. Likewise, the product of spectral subtraction (of absorbance spectra) will include noise from both the reference and sample. In some cases the reference spectrum, for example, water vapour, can be modelled from first principles. In other cases, a noiseless synthetic reference spectrum can be modelled by a least squares fit of analytic functions to the observed reference. In this case caution must be exercised to ensure that all true spectral components are modelled.

The relative spectral contribution of the sample on a complex substrate depends upon the fraction of the sampling area that it occupies. In the preferred embodiments, the pixel size is adjusted so that a contaminant occupies a fraction of at least $1\times10^{-4}$ of the sample area and preferably above $1\times10^{-2}$ of the sample area. As noted above, the beam must be collimated as it passes through the sample multiple times. After the beam exits the sample for the last time, the beam may be focussed by refractive or preferably reflective optics to achieve the required magnification in the detector plane. In one embodiment, the magnification factor is adjustable to facilitate examination of the sample on different length scales.

Examples of suitable optically thin samples include but are by no means limited to bacteria, viruses, cells, animal tissue, plant tissue, polymer blends, micelles, pharmaceutical tablets and silicon wafers.

As discussed above, the method may be used in combination with, for example, a Coulter Counter such that a single cell is deposited on the sample support.

Figure 8:
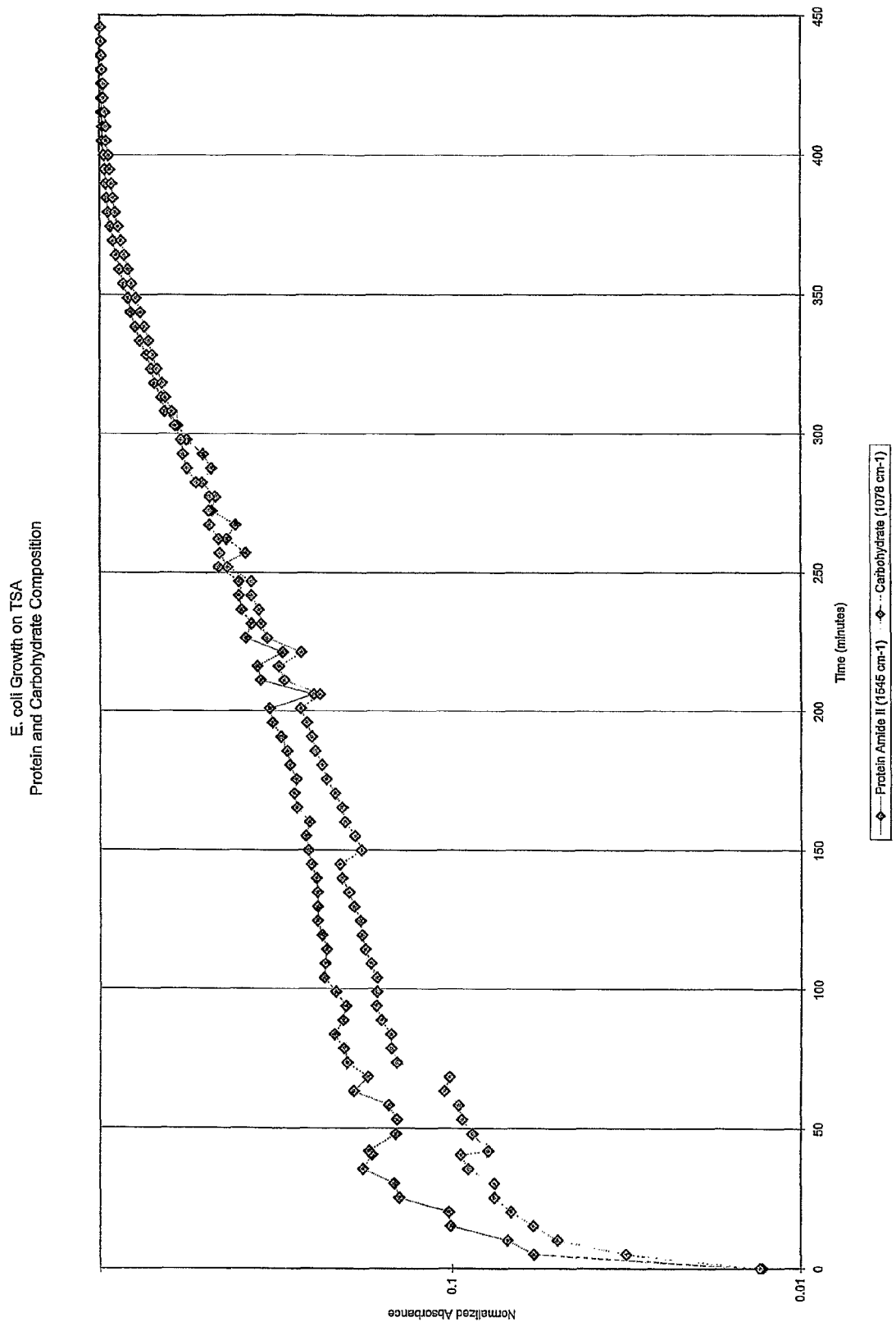
FIG. 8 shows *E. coli* growth on TSA over time.

The above-described method may be used to examine a sample suspected of containing micro-organisms such as bacteria, viruses or fungi, or to identify such micro-organisms in a sample. For example, bacterial species may be determined based on absorbency patterns in the 900-1800 $cm^{-1}$ and 2800-3600 $cm^{-1}$ regions. In one approach, principle component analysis can identify patterns of significant spectral difference among species. The spectral eigenvectors generated by principle component analysis form the basis for cluster analysis to identify unknowns from a database of reference samples. This approach was published by Naumann (1988) and has been used successfully by many others since then. In the present invention, this approach is modified, as discussed below, to include information about the cell mass and the environment from which the sample was taken. Specifically, the cell mass could be included with the spectral data and the environmental information provides the basis to generate a suitable set of reference spectra. In previous studies, the reference spectra were taken under standard conditions in the limit where all absorptions attain constant ratios. FIG. 8 shows the normalized absorption of protein (1545 $cm^{-1}$) and carbohydrate (1078 $cm^{-1}$) of a live *E. coli* culture as a function of time. The relative strengths of these peaks vary with time, likely due to a change in the surface to volume ratio as the average cell mass changes. The cell mass and composition need not be regarded as static, as in the previous approach, but may instead be explicitly modelled as functions of environmental factors. If the environmental factors from which a sample is collected are measured, then the reference spectra for each cell type can be generated based on a model of the mass and composition of the cell for those environmental factors. Alternately, neural networks may be used to do the pattern recognition step. In this case, information about the environment must be included in the training set for the neural network.

In other embodiments, viability of the bacteria may be determined based on absorbency at 1743 $cm^{-1}$ as well as by a shift of the absorbencies due to Amide I and Amide II bonds to lower frequencies (Holman, 2000). As will be appreciated by one of skill in the art, this measurement of viability may be used to examine the effect of new anti-microbial agents or varying concentrations of anti-microbial agents on bacteria, as well as the effects of competitive inhibition on bacteria population ecology. The method can also be used to study the distribution of antibody affinities on the outer surface of a bacterial cell, as well as to study the effects of environment and chemical agents on the metabolism of individual bacteria cells. It is important to note that the instant method does not require amplification or purification of cells for analysis, as discussed herein.

The method could also be used for detecting the presence and identity of viruses within a sample and/or within a cell. As will be appreciated by one skill in the art, this may be based on pattern recognition as discussed above and/or on comparison with a database of previously analyzed samples.

The method could also be used for the classification of cells and to study cell metabolism, as discussed above. That is, changes in metabolism will, of course, have an effect on cell physiology and absorbency.

The method could also be used in combination with animal tissue, for example, for chemical mapping, disease diagnosis, pharmokinetic studies and also for parasite identification, as discussed above. Regarding disease diagnosis, it is of note that diseases such as cancer, Multiple Sclerosis and Alzheimers to name a few, cause physiological changes either in individual cells and/or in the surrounding tissue; these changes would be detected by the instant method, either by pattern recognition or by comparison with a database.

The method could be used in combination with plant tissue for example for chemical mapping, classification, diagnosing diseases, identifying parasites and examining nutrient transport, as discussed herein.

It is of note that bacteria, viruses, cells, animal tissue and plant tissue will typically be examined with wavelengths between 2.5-25 microns.

The method could also be used to analyze micelle preparations, for example, for determining the size and composition of different micelle preparations.

The method could also be used for examining polymer blends, for example, determining phase separation, orientation and crystal domains.

The method could be used to examine pharmaceutical tablets, for example, for detecting contaminants and/or detecting anomalous distributions of ingredients.

The method could also be used for imaging the circuitry of silicon wafers.

It is of note that the analysis of for example silicon wafers and pharmaceutical tablets may be carried out using near-infrared wavelengths.

In one implementation, samples may be spread on standard agar growth media by using standard microbiological techniques. The measurement is made by bringing an internal reflectance element into contact with the agar surface. Prior to the experiment, the IRE is coated with a thin layer of polystyrene (or other suitable polymer) for bio-compatibility. This precaution is necessary because the toxicity of most standard IRE materials could influence the results with live cells. The bacterial, fungal, mammalian, or other cells can be distinguished from the agar by difference spectroscopy. Using this method, it is possible to follow changes in the cells with a time resolution of less than one minute.

Conventional forms or difference spectroscopy either use the first measurement (t=0) as the reference (single beam configuration) or use a reference and a sample (double beam configuration). The E. coli spectra referred to above were collected using the single beam configuration. The primary factor limiting the signal-to-noise ratio achievable in the single beam configuration is the stability of the instrument and the environment proximate to the sample. In the double beam configuration, the problem is matching the optics and the reference and sample substrates closely enough. The present method recognizes that the single beam configuration is equivalent to the double beam configuration if an array detector is used. Specifically, because the sample is optically thin and heterogeneous, there will be many (most likely a majority of) sample regions which are substrate only. If this is not the case, a small portion of the sample surface can be reserved as a reference. A search for those pixels with the largest spectral throughput can identify these reference regions. The substrate can then be interpolated geometrically between reference regions to give a superior estimate of the substrate contribution in regions with sample cells. This method has the advantage that the reference regions are tens of microns from the sample regions and, thus, very closely match the temperature, humidity (perfect water vapour cancellation!), and chemical environment of the sample regions. Using this method, it is possible to measure contaminants even on heterogeneous surfaces such as a tissue sample, provided that the natural variation is at a greater length scale than the contaminant. For example, because mammalian cells are tens of microns in size whereas bacteria are a few microns, this method could, for instance, isolate the spectrum of a bacterium embedded in mammalian tissue.

In another embodiment, bacterial cells may be detected on animal tissue by an increase in the relative magnitude of absorptions between 1000 and 1100 $cm^{-1}$. These absorptions are attributed to carbohydrates in the bacterial cell wall. In a related embodiment, faecal contamination (or ingestia) on bovine, porcine, avian, or similar tissue can be identified on the basis of similar carbohydrate absorptions.

In another embodiment, an aqueous sample is passed through a specially treated filter, leaving a random distribution of cells on the filter surface. The filter is measured immediately after the filtration is complete for between one and five minutes. Both internal and external reflectance methods can be used. Depending upon the environment, it may be necessary to ensure that the sample remains adequately hydrated. The reverse side of the filter could, for instance, be partially immersed in a small reservoir of water (or nutrient broth). Additionally, the filter surface could be overlaid with a transparent (in the spectral region of interest) film. Alternately, the sample region could be enclosed in a constant (100%) humidity chamber with transparent windows. A further variation of the method is to place a very thin <100 nm layer of nutrients on top of the filter.

In yet another embodiment, small droplets containing sample are placed on a metallic film (a tape) in precise positions. An ink jet printer employing piezo technology can be modified for this purpose by using published methods. The impedance of each drop is measured to determine whether there is a cell in the droplet. If there is a cell, the droplet travels to a pre-determined location on the film for measurement. Otherwise, an electronically activated gate blocks the droplet. Information about each sample droplet could also be encoded on the tape by using ink, magnetic, or optical methods. Spectra of a sequence of sample locations are obtained by the cyclic reflectance method.

In the preparation of cell samples, (bacteria for example), there are no requirements for culturing the cells to a pre-defined endpoint. The sensitivity of the method is sufficient to measure the spectral characteristics of single cells. As shown in FIG. 6, the composition of the cells may vary in time according to the growth media used and other environmental conditions. An important cause of variation in cell spectra is the change in surface to volume ratio as the cell size increases. As a cell grows, the protein and nucleic acid-rich interior makes a greater relative spectral contribution than the lipid and carbohydrate rich cell membranes and cell walls. As a cell grows, the total absorbency increases also. By examining both the total absorbency and the spectral distribution of absorption, the cell size may be inferred. Other environmental influences such as light, temperature, pH, nutrients, and bioactive chemicals may also influence the spectra. In many situations, these variables are known, or can be measured independently. Whereas methods for the classification of spectra are well known in the scientific literature, the following discussion outlines only those procedures that are performed in addition to the standard methods. Rather than record a library of sample spectra for each type of cell under one set of standard conditions, reference spectra of each type of single cell is recorded for systematically varied environmental conditions. The range of conditions is chosen to match those conditions expected from which samples will be extracted. For example, if samples will be taken from a human, then a small range of temperatures around 37 C will be sufficient to account for the temperature dependency. The spectrum of each type of cell within the range measured can be modelled by (not necessarily linear) interpolation. For the pattern recognition step of an unknown sample, a reference library is generated from the known environmental conditions. If the cell size is known from an independent measurement of impedance as noted above, this information could be included in the model.

As noted above, cyclic reflectance can be used to measure environmental samples directly by internal reflectance in almost all cases. Internal reflectance measurements require the sample to be in good physical contact with the internal reflection element. As noted above, a thin polymer film coating may be placed on the surface of the internal reflection element in order to improve bio-compatibility. In one embodiment of the sampling procedure the thin polymer film is disposable. Removing the thin polymer film and replacing it with a new polymer film is equivalent to cleaning the IRE between samples. The thin polymer film may be cast from a solvent. Alternately, the thin polymer film may be held between two or more rollers positioned to stretch the thin polymer film over the surface of the internal reflectance element. The contact with the internal reflectance element may be improved in this circumstance by the application of heat. Alternately, the composition of the thin polymer film can be chosen to generate electrostatic forces which aid adhesion.

The internal reflectance method, however, has the drawback that the sampling rate is limited by the time required for the cleaning procedure. For experiments which measure cellular changes over time, the internal reflectance method may not be suitable where aerobic conditions are required. In these cases, the external reflectance method must be used. As noted above, the effectiveness of cyclic reflectance depends upon the reflectivity of the sample substrate. If the reflectivity of the sample substrate is low (<90%), it may be desirable to remount sample cells on a more reflective substrate. Cells may be removed from an environmental surface by the application of a stream of water, or other suitable fluid, at a sufficient pressure to overcome cellular adhesion forces The pressure required may range from less than 1 dyne/cm$^2$ to more than 200 dyne/cm$^2$, depending upon the type of cells and the initial substrate. The cells so dislodged can be collected by an aspirator and deposited on a reflective surface by any of the methods discussed above for liquid samples. This method has the advantages that samples can be collected from any surface, even from inside small cracks. Suitable surfaces include, but are by no means limited to, floors, ceilings, walls, counter tops, sinks, drainage pipes, food processing equipment, medical instruments, animal carcases, fruits, vegetables, and humans. One can appreciate that it is possible to classify cells by both their adhesion characteristics and by their spectral characteristics by using this method.

In one embodiment, an internal reflection cyclic reflectance element may be used for real-time tissue mapping during a surgical procedure.

While the preferred embodiments of the invention have been described above, it will be recognized and understood that various modifications may be made therein, and the appended claims are intended to cover all such modifications which may fall within the spirit and scope of the invention.

The invention claimed is:

1. A method of analyzing an optically thin sample comprising:
   a) providing an optically thin sample and an optical system, said optical system comprising at least one optical probe arranged to emit a collimated ray, at least one detector and a detector plane and said sample being within the optical system, thereby defining a sample plane;
   b) constructing an n×m C matrix based on said sample, wherein (n) rows represent logical detector regions and (m) columns represent sample regions by dividing the detector plane into n logical regions with a coordinate system commensurate with the optical system, and dividing the sample plane into m regions;
   c) propagating a collimated ray through the optical system from each vertex on the sample plane such that said ray is directed through the sample and then reflected back through the sample one or more times, and noting the coordinates each time the sample surface is intersected, wherein angle of incidence for the ray is the same for each sample pass;
   d) for each set of sample plane intersections from (c), execute steps (e) and (f);
   e) for each row representing a detector region, execute step (f);
   f) for each sample region, calculating the fraction of the sample region that lies within the detector region;
   g) adding each value obtained in step (f) for each sample region to the value in the column of the C matrix for that sample region;
   h) calculating the inverse of the C matrix; and
   i) calculating the distribution of absorbency in the optically thin sample using the inverse of the C matrix and a column vector of absorption measured by each detector.

2. The method according to claim 1 wherein the sample is mounted to a reflective surface.

3. The method according to claim 2 wherein the reflective surface is selected from the group consisting of Au, Ag, Cu, Al and Ni.

4. The method according to claim 1 wherein the optically thin sample is selected from the group consisting of bacteria, viruses, cells, animal tissue, plant tissue, micelles, polymer blends, pharmaceutical tablets and silicon wafers.

5. The method according to claim 1 wherein the angle of incidence is between 30 to 60 degrees.

6. The method according to claim 1 wherein the ray is reflected back through the sample until the absorbency is between 0.1 to 1.0 absorbency units.

7. The method according to claim 1 wherein the detector is a focal plane array.

8. The method according to claim 1 wherein the detector is a virtual detector array.

9. The method according to claim 1 wherein constituents present in a sample region are identified by comparing the distribution of absorbency to a database.

10. The method according to claim 1 wherein the sample is identified by analyzing the distribution of absorbency of the sample for identifiable patterns.

11. The method according to claim 1 including:
j) reconstructing the image by linear transformation.

12. The method according to claim 1 wherein the matrix is made non-singular by establishing sample regions contributing zero absorbency as boundaries.

13. The method according to claim 1 wherein the sample is deposited on an optically transparent substrate held between two reflective surfaces.

14. The method according to claim 1 wherein the sample is entrained in or suspended by an optically transparent gas or liquid.

15. The method according to claim 14 wherein the sample is gaseous.

16. The method according to claim 1 wherein the sample is on a substrate that has been metalized in colloid form.

17. The method according to claim 13 wherein the optically transparent substrate is selected from the group consisting of alkali halide salts, glasses, very thin polymer films and aerogels.

18. The method according to claim 1 wherein the C matrix is sampled using a sampling scheme based on space groups.

19. The method according to claim 1 wherein the C matrix is sampled using a sampling scheme based on Penrose patterns.

20. The method according to claim 1 wherein the sample is deposited onto a reflective strip of film.

21. The method according to claim 20 wherein the film includes information about the sample and the film location proximate to sites of sample deposition.

22. The method according to claim 1 wherein the sample is held in position by electromagnetic forces.

23. The method according to claim 1 wherein the sample is an individual cell in a small water droplet separated from a suspension of cells.

24. The method according to claim 23 wherein the individual cell is separated from the suspension of cells by an apparatus comprising a gate which opens to deposit the cell on a reflective tape at a precisely determined region of the tape.

25. The method according to claim 24 wherein the tape is encoded with information on the mass of the cell, environment of the cell and a unique identifier at a location proximate to the cell deposited on the tape.

26. The method according to claim 1 wherein the sample is a bacterial cell detected on animal tissue by an increase in magnitude of absorptions between 1000 and 1100 $cm^{-1}$.

27. The method according to claim 1 wherein the sample is faecal contamination detected on animal tissue by an increase in magnitude of absorptions between 1000 and 1100 $cm^{-1}$.

28. The method according to claim 1 wherein the sample is a cell and the spatial distribution of absorption and total absorbency are used to infer cell size.

29. The method according to claim 1 wherein reference spectra of a cell is recorded systematically for varied environmental conditions.

30. The method according to claim 1 wherein the sample is mounted onto a thin polymer film.

31. The method according to claim 30 wherein the thin polymer film is disposable.

32. The method according to claim 30 wherein the thin polymer film is held between two or more rollers.

33. The method according to claim 30 wherein the thin polymer film generates electrostatic forces for adhesion of the sample to the thin polymer film.

34. The method according to claim 23 wherein the suspension of cells is removed from a surface by applying a stream of a suitable fluid at a pressure between less than 1 $dyne/cm^2$ to more than 200 $dyne/cm^2$.

35. The method according to claim 1 wherein the distribution of absorbency is used as a basis for computed tomography (CT) calculations.

* * * * *